United States Patent
Myers (10) Patent No.: US 6,473,632 B1
(45) Date of Patent: Oct. 29, 2002

(54) TOTAL HEMOGLOBIN CONCENTRATION MEASUREMENT

(75) Inventor: Dean E. Myers, Stewart, MN (US)

(73) Assignee: Hutchinson Technology Incorporated, Hutchinson, MN (US)

(*) Notice: Subject to any disclaimer, the term of this patent is extended or adjusted under 35 U.S.C. 154(b) by 18 days.

(21) Appl. No.: 09/595,148

(22) Filed: Jun. 16, 2000

Related U.S. Application Data (60) Provisional application No. 60/139,552, filed on Jun. 16, 1999.

(51) Int. Cl.⁷ ................................................ A61B 5/00
(52) U.S. Cl. ........................ 600/322; 600/328; 600/331
(58) Field of Search .................... 600/309–311, 316, 600/322–324, 328, 331

(56) References Cited

U.S. PATENT DOCUMENTS

| | | | | |
|---|---|---|---|---|
| 4,875,486 A | * | 10/1989 | Rapoport et al. | 600/415 |
| 5,308,982 A | | 5/1994 | Ivaldi et al. | 250/339.01 |
| 5,361,758 A | * | 11/1994 | Hall et al. | 600/322 |
| 5,377,674 A | | 1/1995 | Kuestner | |
| 5,729,333 A | | 3/1998 | Osten et al. | 356/39 |
| 5,879,294 A | | 3/1999 | Anderson et al. | 600/310 |
| 5,931,779 A | * | 8/1999 | Arakaki et al. | 600/310 |
| 5,978,691 A | | 11/1999 | Mills | 600/334 |
| 6,006,119 A | | 12/1999 | Soller et al. | 600/322 |

FOREIGN PATENT DOCUMENTS

EP 0 816 829 1/1998

OTHER PUBLICATIONS

PCT International Search Report PCT/US00/16589 mailed Oct. 2, 2000 (7 pages).

* cited by examiner

*Primary Examiner*—Eric F. Winakur
*Assistant Examiner*—Matthew Kremer
(74) *Attorney, Agent, or Firm*—Faegre & Benson LLP (57) ABSTRACT

A method for operating a spectrophotometric instrument of the type for measuring the oxygenation state of hemoglobin in tissue. The method includes the use of stored hemoglobin concentration relationship data characterizing the relationship between second derivative absorbance values at a hemoglobin-absorbing wavelength and hemoglobin concentration in a tissue as a function of hemoglobin oxygenation state. Data representative of a second derivative absorbance value of tissue being analyzed is received. The hemoglobin oxygenation state of the tissue is determined as a function of the second derivative absorbance value. The hemoglobin concentration in the tissue is then determined as a function of the hemoglobin concentration relationship data, the second derivative absorbance value and the hemoglobin oxygenation state. The accuracy of the hemoglobin oxygenation state can be determined as a function of the hemoglobin concentration value.

20 Claims, 7 Drawing Sheets

| %StO2 | 2nd680/2nd720 | Hct Slope (Mso2) | %StO2 | 2nd680/2nd720 | Hct Slope (Mso2) |
|---|---|---|---|---|---|
| 0 | -1.166 | 22.56 | 50 | -1.670 | 44.28 |
| 1 | -1.175 | 22.78 | 51 | -1.684 | 45.15 |
| 2 | -1.184 | 23.01 | 52 | -1.699 | 46.06 |
| 3 | -1.194 | 23.24 | 53 | -1.713 | 47.00 |
| 4 | -1.203 | 23.48 | 54 | -1.727 | 47.98 |
| 5 | -1.212 | 23.72 | 55 | -1.741 | 49.00 |
| 6 | -1.221 | 23.97 | 56 | -1.755 | 50.07 |
| 7 | -1.230 | 24.22 | 57 | -1.770 | 51.19 |
| 8 | -1.239 | 24.48 | 58 | -1.784 | 52.35 |
| 9 | -1.249 | 24.75 | 59 | -1.798 | 53.57 |
| 10 | -1.258 | 25.01 | 60 | -1.812 | 54.85 |
| 11 | -1.267 | 25.29 | 61 | -1.826 | 56.19 |
| 12 | -1.276 | 25.57 | 62 | -1.841 | 57.60 |
| 13 | -1.285 | 25.86 | 63 | -1.855 | 59.08 |
| 14 | -1.294 | 26.15 | 64 | -1.869 | 60.64 |
| 15 | -1.304 | 26.45 | 65 | -1.883 | 62.28 |
| 16 | -1.313 | 26.76 | 66 | -1.897 | 64.02 |
| 17 | -1.322 | 27.08 | 67 | -1.921 | 65.85 |
| 18 | -1.331 | 27.40 | 68 | -1.932 | 67.80 |
| 19 | -1.340 | 27.73 | 69 | -1.954 | 69.86 |
| 20 | -1.349 | 28.07 | 70 | -1.990 | 72.05 |
| 21 | -1.359 | 28.41 | 71 | -2.050 | 74.38 |
| 22 | -1.368 | 28.77 | 72 | -2.080 | 76.87 |
| 23 | -1.377 | 29.13 | 73 | -2.120 | 79.54 |
| 24 | -1.386 | 29.51 | 74 | -2.150 | 82.39 |
| 25 | -1.395 | 29.89 | 75 | -2.190 | 85.46 |
| 26 | -1.404 | 30.29 | 76 | -2.230 | 88.76 |
| 27 | -1.414 | 30.69 | 77 | -2.270 | 92.33 |
| 28 | -1.423 | 31.10 | 78 | -2.310 | 96.20 |
| 29 | -1.432 | 31.53 | 79 | -2.350 | 100.42 |
| 30 | -1.441 | 31.97 | 80 | -2.400 | 105.01 |
| 31 | -1.450 | 32.42 | 81 | -2.450 | 110.05 |
| 32 | -1.459 | 32.88 | 82 | -2.500 | 115.60 |
| 33 | -1.469 | 33.36 | 83 | -2.550 | 121.75 |
| 34 | -1.478 | 33.85 | 84 | -2.600 | 128.58 |
| 35 | -1.487 | 34.36 | 85 | -2.660 | 136.24 |
| 36 | -1.496 | 34.88 | 86 | -2.730 | 144.86 |
| 37 | -1.505 | 35.42 | 87 | -2.800 | 154.66 |
| 38 | -1.514 | 35.97 | 88 | -2.880 | 165.90 |
| 39 | -1.524 | 36.54 | 89 | -2.960 | 178.91 |
| 40 | -1.533 | 37.13 | 90 | -3.050 | 194.16 |
| 41 | -1.542 | 37.74 | 91 | -3.150 | 212.28 |
| 42 | -1.557 | 38.37 | 92 | -3.270 | 234.19 |
| 43 | -1.571 | 39.02 | 93 | -3.400 | 261.23 |
| 44 | -1.585 | 39.70 | 94 | -3.580 | 295.49 |
| 45 | -1.599 | 40.39 | 95 | -3.750 | 340.40 |
| 46 | -1.613 | 41.12 | 96 | -4.040 | 402.03 |
| 47 | -1.628 | 41.86 | 97 | -4.500 | 492.44 |
| 48 | -1.642 | 42.64 | 98 | -5.510 | 639.77 |
| 49 | -1.656 | 43.45 | 99 | -9.650 | 931.66 |

TOTAL HEMOGLOBIN CONCENTRATION MEASUREMENT

REFERENCE TO RELATED APPLICATION

This application claims the benefit of U.S. Provisional Application Serial No. 60/139,552 filed on Jun. 16, 1999, and entitled "Total Hemoglobin Concentration Measurement," which is incorporated herein by reference.

FIELD OF THE INVENTION

The present invention relates generally to methods and instruments for measuring the concentration of a chromophore such as hemoglobin in tissue.

BACKGROUND OF THE INVENTION

Spectrophotometric instruments and methods for measuring the amount of a tissue chromophore having a certain functional state (e.g., the percentage of oxidized hemoglobin or StO2, and the percentage of oxidized cytochrome aa3) are generally known and disclosed, for example, in the Anderson et al. U.S. Pat. No. 5,879,294, which is hereby incorporated by reference in its entirety. The Anderson et al. patent discloses in particular a measurement algorithm which makes use of scaled second derivative spectrum values.

The Kuestner U.S. Pat. No. 5,377,674 discloses a spectrophotometric instrument and method for measuring the total concentration of a chromophore such as hemoglobin in tissue. The measurement algorithm uses a single term ratio of second derivative absorbance measured at a wavelength at which hemoglobin absorption occurs (analyte wavelength), and a second derivative absorbance measured in a wavelength region where no hemoglobin absorption occurs (reference wavelength) (e.g, $2^{nd}$ derivative of absorbance at 1740 nm / $2^{nd}$ derivative of absorbance at 1346 nm).

There remains, however, a continuing need for improved instruments and methods for measuring the total concentration of chromophores such as hemoglobin in tissue.

BRIEF DESCRIPTION OF THE DRAWINGS

FIG. 5 is an example of a lookup table of data derived from the data shown in FIG. 4 and describing the relationship between hemoglobin oxidation state and hematocrit levels.

SUMMARY OF THE INVENTION

A method for measuring the total concentration of a chromophore, such as hemoglobin, in tissue. The method includes providing stored relationship data characterizing the relationship between second derivative absorbance values at a chromophore-absorbing wavelength and the concentration of the chromophore in the tissue. Data representative of a measured second derivative absorbance value from tissue being analyzed is received. Data representative of the chromophore concentration can then be generated as a function of the second derivative absorbance value and the stored relationship data. In one embodiment of the invention, the measured chromophore concentration can be used to evaluate the accuracy of measurements of a functional state of the chromophore (e.g., the oxygenation state of the hemoglobin).

DETAILED DESCRIPTION OF THE INVENTION

The invention is an instrument and method for using the combination of both a single term ratio of a second derivative absorbance value and a single term non-ratioed second derivative value to measure the volume percentage of a chromophore such as hemoglobin in tissue (a value that directly correlates with hemoglobin concentration). The wavelengths used by the method are all within a region where hemoglobin absorption takes place. There is no requirement for a "reference wavelength" which occurs in a region where hemoglobin absorption does not take place. An advantage of the invention is that the spectral region from 680 nm to 800 nm can be used to measure hemoglobin concentration. In this wavelength region the oxygenation state of hemoglobin (%StO2) (i.e., a portion of the chromophore having a particular functional state) is a factor which must be considered when making total hemoglobin concentration measurements using derivative spectroscopy. The utilization of both a single term derivative ratio (which varies with %StO2) and a non-ratioed second derivative term (which varies with %StO2 and total hemoglobin concentration) provides a means to distinguish hemoglobin concentration separately from the amount of oxidized hemoglobin. The non-ratioed second derivative term (at 720 nm in the embodiment described herein) is also used in the denominator of the ratioed second derivative term. Both hemoglobin oxidation percentage and total hemoglobin concentration percentage can be obtained with a minimum of wavelength specific absorbance measurements (e.g., 4 wavelengths are used in the instrument disclosed in the Anderson et al. patent).

In one configuration the wavelength gap used to calculate the second derivative values (i.e., the interval between adjacent absorbance wavelengths used in the second derivative calculation) is 40 nm. At this gap size only four wavelengths are used to calculate both the percentage of oxidized hemoglobin and the percentage of total hemoglobin in the tissue (% hematocrit). The second derivative absorbance peak at 720 nm (deoxyhemoglobin absorption band of 760 nm) is used to empirically derive the relationship between percent hematocrit and second derivative absorbance. Second derivative gap sizes other than 40 nm can also be used to derive the hematocrit algorithm. Also, other wavelength regions (e.g., visible or infrared) corresponding to other oxyhemoglobin or deoxyhemoglobin absorbance maximums could be used.

The total hemoglobin concentration measurements made in accordance with the algorithms described herein can be used by an instrument in connection with tissue recognition algorithms. Inaccurate and/or invalid measurements of %StO2 or other measured parameters can be displayed by the instrument monitor if the probe is not properly located on the tissue to be measured. The total hemoglobin concentration measurement can be used by the instrument to determine whether the probe is properly positioned and the measurement is accurate. For example, in connection with some or all of the parameter measurements, the instrument can compute the total hemoglobin concentration using the algorithm described herein, and display the parameter measurement as an accurate measurement only if the hemoglobin concentration measurement is representative of a predetermined minimum level. If the hemoglobin concentration measurement is below the predetermined level, the monitor can generate a display indicating that the probe is not properly positioned.

Total hemoglobin concentration measurements in accordance with the invention can be generated as a function of current second derivative spectroscopy values and stored data describing the relationship between the second derivative values and the total hemoglobin concentration. In the embodiment described below, the stored relationship data is data describing a set of lines or slopes (or curves if preferred), each of which is associated with a constant oxidation state of hemoglobin.

During total hemoglobin concentration measurements, the proper stored relationship data can be selected by the instrument on the basis of the measured hemoglobin oxidation state. From this data and the current second derivative spectroscopy value, the total hemoglobin concentration can be computed by the instrument.

Figure 1:
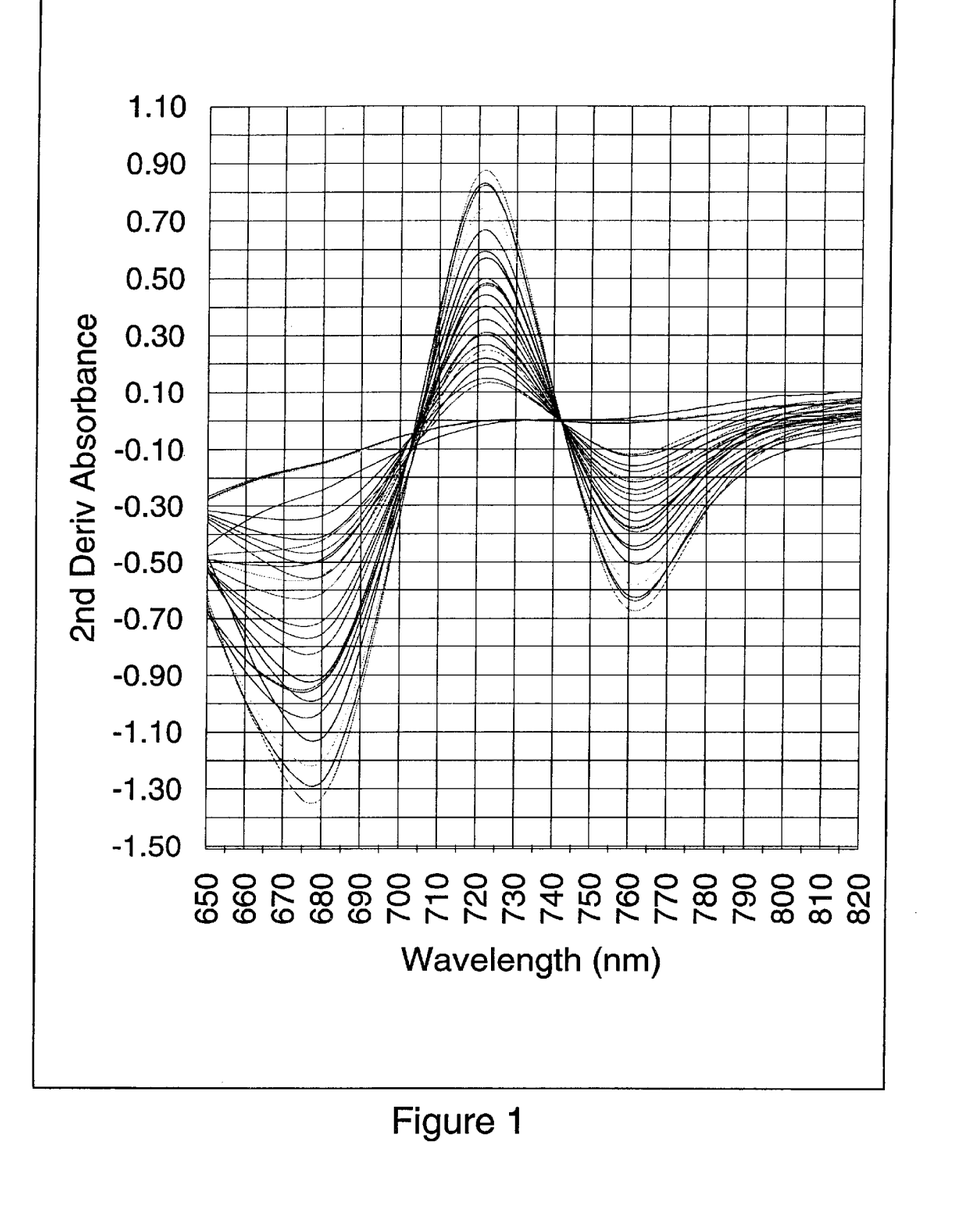
FIG. 1 is a graph of an example of measured bovine blood second derivative absorbance values as a function of wavelength at a range of conditions of oxyhemoglobin optical density.

Stored second derivative/hemoglobin concentration relationship data can be generated in the following manner. FIG. 1 is a graph of measured second derivative (40 nm gap) spectra of bovine blood at a range of conditions of oxyhemoglobin optical density. The shape transformation of the illustrated spectra (e.g., peak height at 720 nm) is influenced by three primary factors (%StO2, % hematocrit and optical path length). The height of the second derivative absorbance values shown in FIG. 1 varies directly with hemoglobin concentration and inversely with the hemoglobin oxidation state. To determine the % hematocrit from unsealed second derivative features, both the %StO2 and path length need to be defined.

Figure 2:
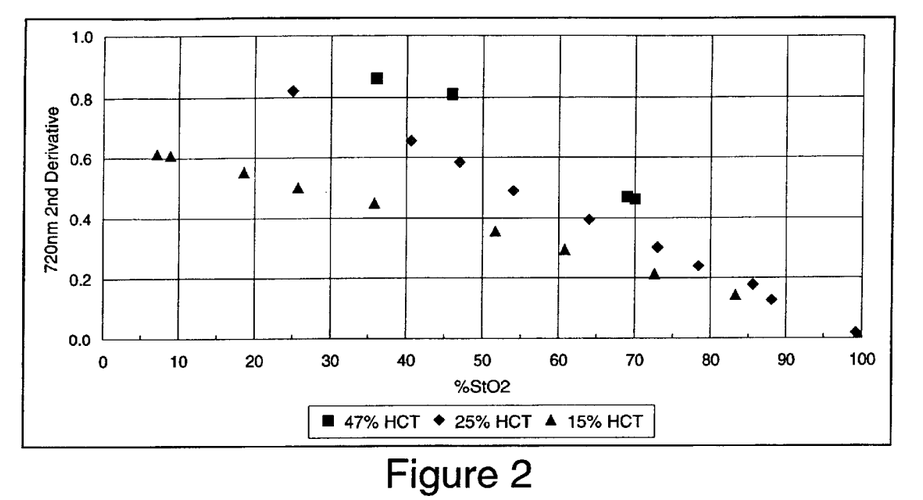
FIG. 2 is a graph of an example of measured bovine blood second derivative absorbance value data points as a function of hemoglobin oxidation state at hematocrit levels of 47%, 25% and 15%.
Figure 3:
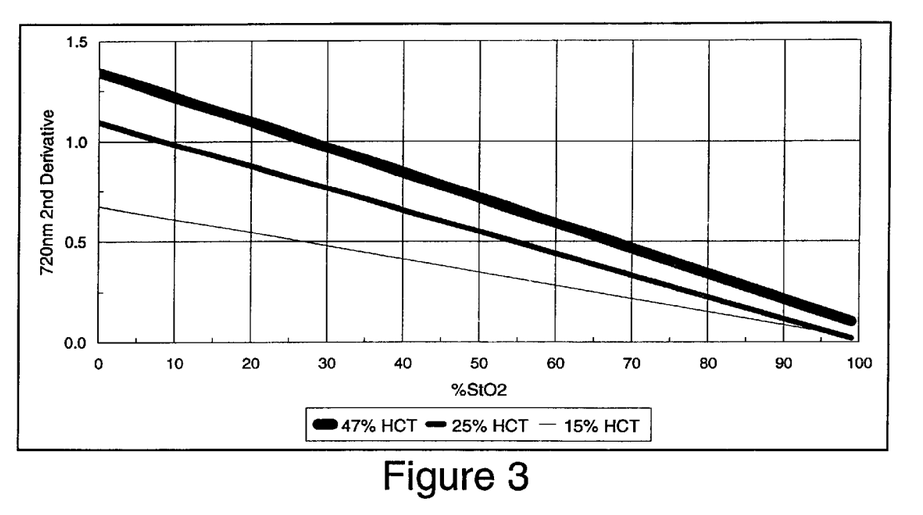
FIG. 3 is a graph of lines fitted to the data points shown in FIG. 2.

At multiple levels of hematocrit (HCT), the second derivative spectral features of the blood are recorded at a predetermined (e.g., 5 mm) probe spacing over multiple % StO2 values within the 0%–100% range as illustrated in FIG. 2. For each hematocrit the 720 nm second derivative peak is fitted to a linear equation as is illustrated in FIG. 3.

Figure 4:
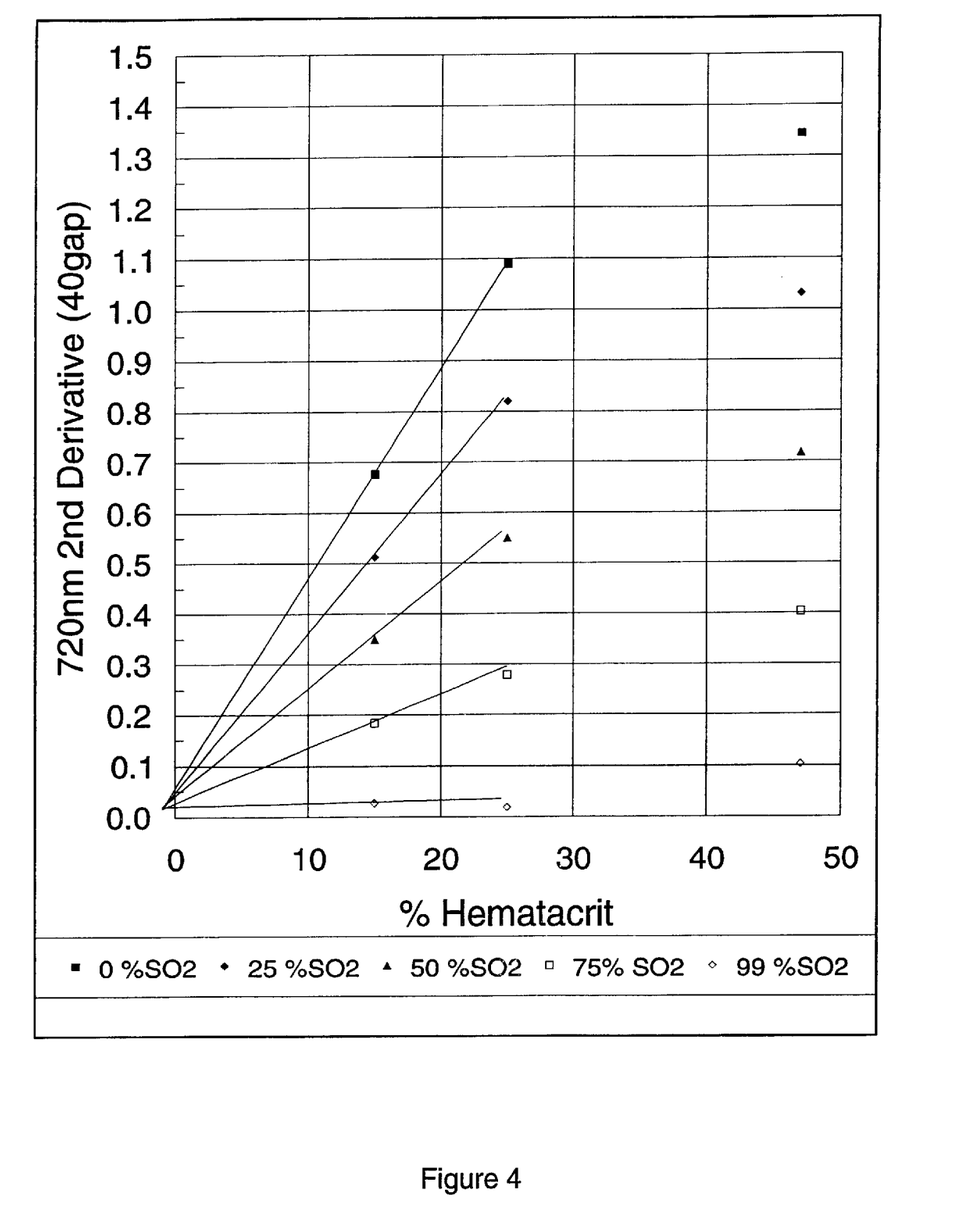
FIG. 4 is a graph of bovine blood second derivative absorbance values as a function of hematocrit concentrations derived from the data shown in FIG. 3 at hemoglobin oxidation (i.e., functional) states of 0%, 25%, 50%, 75% and 99%.

At each constant level of %StO2, the second derivative 720 nm feature is related to % hematocrit with extrapolation to 0% hematocrit. As illustrated in FIG. 4, from this step it is evident that there is a linear relationship between the 720 nm second derivative and hematocrit at hematocrits of about 25% and less.

Figure 6:
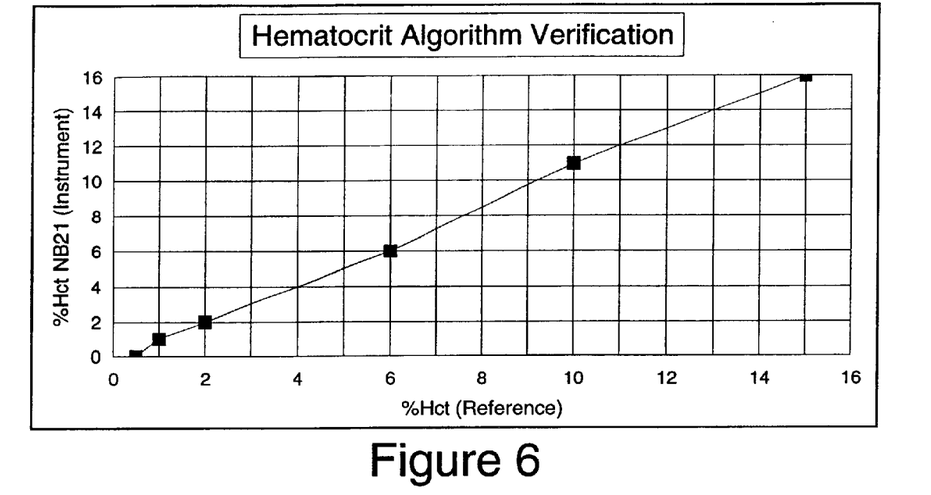
FIG. 6 is a graph of data showing the correlation between hematocrit measurements made using the described invention and a reference method by which a centrifuged Wintrobe tube is used to measure the height of packed red blood cells relative to the total sample height (red blood cells and plasma).
Figure 7:
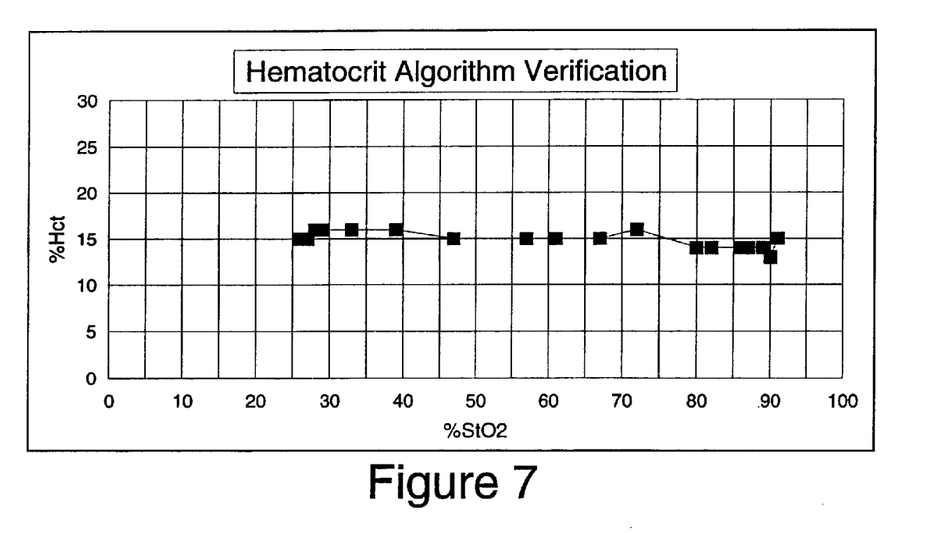
FIG. 7 is a graph of test data showing the correlation between hematocrit measurements made using the described invention in which hemoglobin oxidation state was varied while hematocrit levels remain constant.

Using linear extrapolation to 0% hematocrit and empirical measurements at 25% and 15% hematocrit, a lookup table of relationship data which describes the sensitivity of hematocrit to the 720 nm second derivative values (lines of constant %StO2) can be created as illustrated in FIG. 5. The slopes are functionally related to the ratio of the second derivative at 680 nm to the second derivative at 720 nm. FIGS. 6 and 7 are graphs of several verification exercises (tests) performed for the algorithm described above.

To compensate for measurements made with probe spacings other than that used to generate the relationship data, a probe scaling factor (PSF) which relates the relative change in path length due to probe spacing is used to adjust the 720 nm second derivative values.

The stored relationship data described above is subsequently used during total hemoglobin concentration measurements. Upon measuring %StO2 (e.g., using conventional algorithms and scaled second derivative values at 680 nm) the corresponding slope value (Mso2 or hct slope) is found within the lookup table. The predicted hematocrit value is then:

$$\%Hct = Mso2 \times D720/PSF$$

Where: D720 is the second derivative at 720 nm using the 40 nm gap PSF is the relative path length change due to probe spacing The concentration of tissue hematocrit is generally less than 25%, and is usually in the 1%–10% range. When evaluating probe position on the basis of hemoglobin concentration measurements, relatively high measurement accuracy near the lower end of the range is sufficient. For example, the threshold for determining whether the probe is on or off tissue can be in the range of 1% measured hemoglobin concentration. The linear range of spectral features versus hematocrit concentration (e.g., less than about 25% in FIG. 4) need only be used for this application. However, in accordance with the present invention, the measurement accuracy can be extended to greater percentages of hematocrit by redefining the algorithm to account for nonlinearities. The algorithm could, for example, be redefined as a multiple regression algorithm consisting of multiple slope and second derivative transformations (linear transformations). Examples of nonlinear equations include:

$$\%Hct = Mso2_1 \times (D720/PSF) + Mso2_2 \times Log(D720/PSF)$$

or $$\%Hct = Mso2_1 \times (D720/PSF) + Mso2_2 \times (D720/PSF)^{1/2} + Mso2_3 \times (D720/PSF)^{1/3+}$$

Where: $Mso2_1$, $Mso2_2$, . . . are nonlinear slope value coefficients which can be stored in the lookup table.

Figure 8:
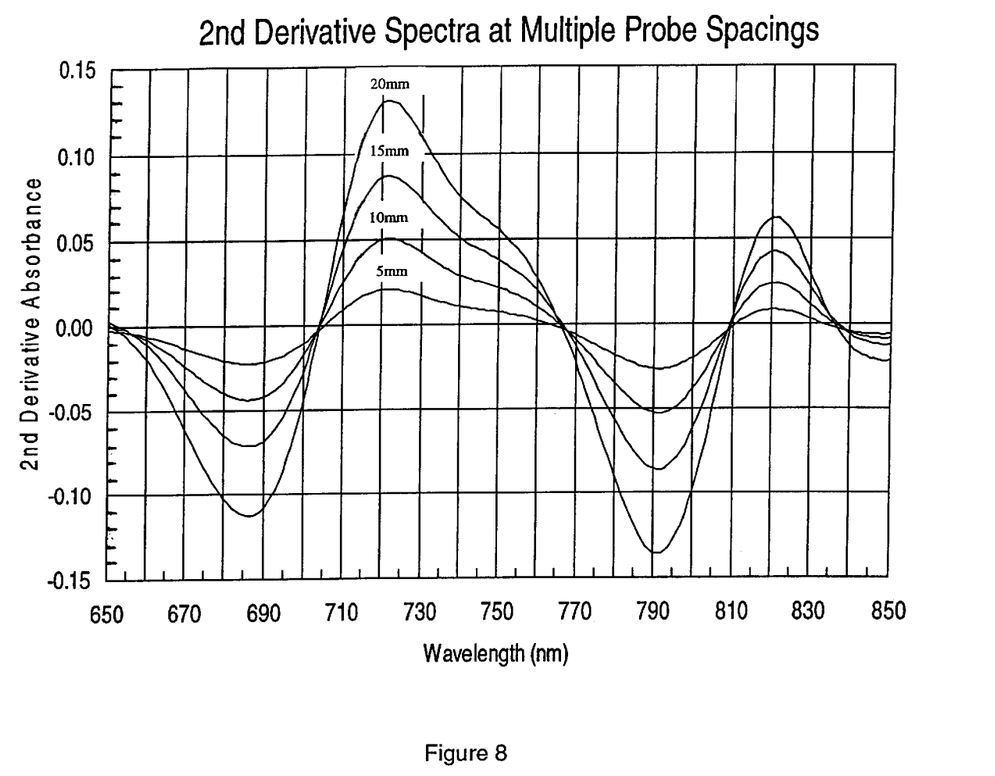
FIG. 8 is a graph of an example of measured second derivative absorbance value data points as a function of wavelength at probe send-to-receive fiber spacings of 5 mm, 10 mm, 15 mm and 20 mm.
Figure 9:
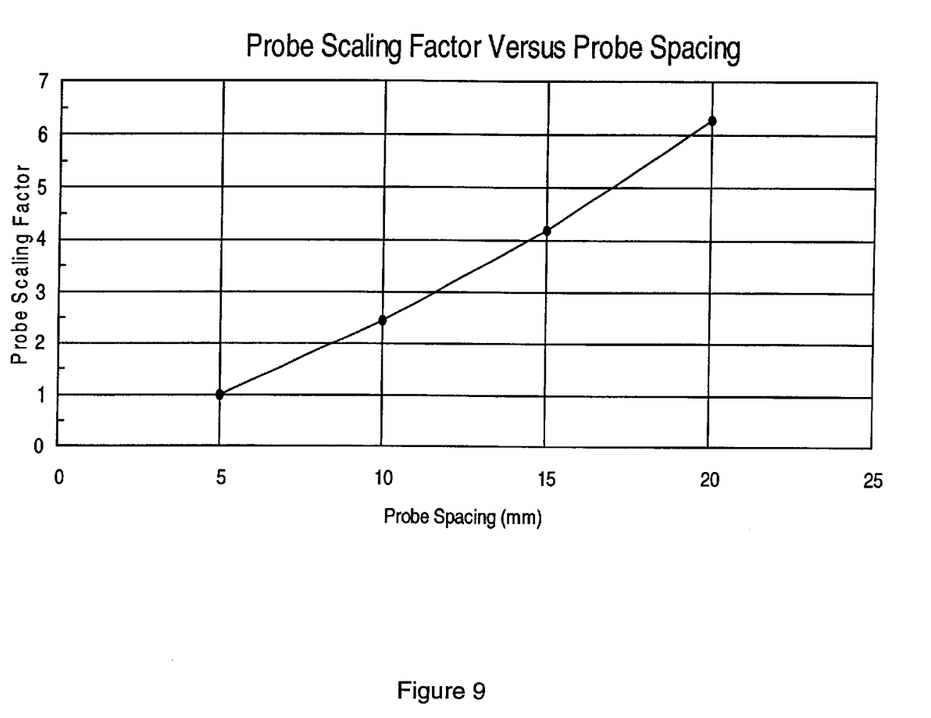
FIG. 9 is a graph of an example of probe scaling factors (PSF) as a function of probe spacing derived from the data shown in FIG. 8 and referenced to a spacing of 5 mm.

The probe scaling factor (PSF) can be empirically determined by collecting second derivative spectral measurements of a chromophore medium, preferably having constant scattering and absorption properties, with optical probes having variable distances between the optical send and receive fibers. The spectral measurements at each probe spacing are then referenced (ratioed) to one of the fixed probe spacing spectral measurements at a particular wavelength of interest. The ratio of one second derivative spectrum value at a probe spacing of interest to the second derivative spectrum value of the reference probe spacing then reflects the probe scaling factor. FIG. 8 is a graph of second derivative spectra measured at 4 different probe spacings. The medium used to obtain the data in FIG. 8 was a 2.5% aqueous solution of 1 micron polystyrene microspheres. FIG. 9 represents the probe scaling factor measured from the ratio of second derivative spectrum values at approximately 725 nm (the absorbance peak in FIG. 8). The following equation represents an example calculation of the probe scaling factor from the spectral information in FIG. 9:

$$\text{PSF (20 mm probe)} = \frac{725 \text{ nm } 2^{\text{nd}} \text{ derivative value (20 mm probe)}}{725 \text{ nm } 2^{\text{nd}} \text{ derivative value (5 mm probe)}}$$

The denominator in the equation represents the reference probe spacing (the probe spacing used to create the hemoglobin concentration algorithm). This probe scaling factor allows the hemoglobin concentration algorithm to be used with probe designs other than the 5 mm probe for which the algorithm is empirically created.

Although the present invention has been described with reference to preferred embodiments, those skilled in the art will recognize that changes can be made in form and detail without departing from the spirit and scope of the invention.

What is claimed is:

1. A method for measuring total concentration of a chromophore having at least two functional states in tissue, including:
    providing stored relationship data representative of lines or curves which characterize the relationship between second-derivative absorbance values at a first chromophore-absorbing wavelength and total concentration of the chromophore in tissue at constant functional state portion values;
    receiving a first second-derivative absorbance value from a tissue being analyzed at the first chromophore-absorbing wavelength;
    receiving functional state portion data representative of the value of the functional state portion of the chromophore in the tissue being analyzed; and
    generating data representative of the total concentration of the chromophore in the tissue being analyzed as a function of the line or curve of constant functional state portion of the chromophore associated with the received functional state portion data and the received first second-derivative absorbance value.

2. The method of claim 1, wherein the chromophore is hemoglobin, and wherein:
    providing the stored relationship data includes providing data representative of lines or curves of constant %StO2;
    receiving functional state portion data includes receiving data representative of a %StO2 portion value; and
    generating data representative of the total concentration of hemoglobin includes generating the data as a function of the line or curve of constant %StO2 associated with the received data representing the %StO2 portion value and the received first second-derivative absorbance value.

3. The method of claim 2, wherein the first chromophore-absorbing wavelength is 760 nm.

4. The method of claim 2, wherein the data representative of the %StO2 portion value includes a second second-derivative absorbance value at a second chromophore-absorbing wavelength.

5. The method of claim 4, wherein the data representative of the %StO2 portion value includes a ratio of the second second-derivative absorbance value over the first second-derivative absorbance value.

6. The method of claim 4, wherein the second chromophore-absorbing wavelength is 720 nm.

7. The method of claim 6, wherein the first and second second-derivative absorbance values are calculated from absorbance values measured at each of 680 nm, 720 nm, 760 nm, and 800 nm.

8. The method of claim 2, and further including the step of:
    determining validity of the %StO2 portion value as a function of the data representative of the total concentration of hemoglobin.

9. The method of claim 8, and further including the step of:
    providing a display indicating the validity of the %StO2 portion value.

10. The method of claim 1 wherein the functional state portion data includes a second second-derivative absorbance value at a second chromophore-absorbing wavelength.

11. The method of claim 10, wherein the functional state portion data includes a ratio of the first second-derivative absorbance value and the second second-derivative absorbance value.

12. The method of claim 1, further including the step of:
    determining validity of the functional state portion data as a function of the data representative of the total concentration of the chromophore.

13. The method of claim 12, further including the step of:
    providing a display indicating the validity of the functional state portion data.

14. A spectrophotometic instrument for generating data representative of the total concentration of a chromophore in accordance with the method of claim 1.

15. The instrument of claim 14, configured to measure absorbance values at each of 680 nm, 720 nm, 760 nm and 800 nm.

16. A method for operating a spectrophotometric instrument of the type for measuring oxygenation state of hemoglobin in tissue, including:
    providing stored hemoglobin concentration relationship data characterizing the relationship between second-derivative absorbance values at a first hemoglobin-absorbing wavelength and hemoglobin concentration in tissue as a function of hemoglobin oxygenation state;
    receiving a first second-derivative absorbance value at the first hemoglobin-absorbing wavelength from a tissue being analyzed;
    determining hemoglobin oxygenation state of the tissue being analyzed; and
    determining the hemoglobin concentration in the tissue being analyzed as a function of the hemoglobin concentration relationship data, the first second-derivative absorbance value and the hemoglobin oxygenation state.

17. The method of claim 16, wherein the first hemoglobin-absorbing wavelength is 760 nm.

18. The method of claim 16, wherein determining the hemoglobin oxygenation state includes receiving a second second-derivative absorbance value from the tissue being analyzed at a second hemoglobin-absorbing wavelength.

19. The method of claim 18, wherein the second hemoglobin-absorbing wavelength is 720 nm.

20. The method of claim 18, wherein determining the hemoglobin oxygenation state includes calculating a ratio of the second second-derivative absorbance value over the first second-derivative absorbance value.

* * * * *